United States Patent [19]

Ruppert et al.

[11] Patent Number: 4,992,582
[45] Date of Patent: Feb. 12, 1991

[54] METHOD FOR MAKING ISOBUTYRIC ACID

[75] Inventors: Wolfgang Ruppert, Bickenbach; Hermann-Josef Siegert, Seeheim-Jugenheim, both of Fed. Rep. of Germany

[73] Assignee: Röhm GmbH, Darmstadt, Fed. Rep. of Germany

[21] Appl. No.: 287,895

[22] Filed: Dec. 20, 1988

[30] Foreign Application Priority Data

Jan. 11, 1988 [DE] Fed. Rep. of Germany ....... 3800473

[51] Int. Cl.$^5$ .............................................. C07C 51/14
[52] U.S. Cl. ...................... 562/521; 203/88; 203/91
[58] Field of Search ...................... 562/521; 203/91, 88

[56] References Cited

FOREIGN PATENT DOCUMENTS 0031886 7/1981 European Pat. Off. .
0324360 7/1989 European Pat. Off. ............ 562/521
WO83/02940 9/1983 PCT Int'l Appl. .

Primary Examiner—Werren B. Lone
Attorney, Agent, or Firm—Curtis, Morris & Safford

[57] ABSTRACT

In the continuous preparation of isobutyric acid by the Koch synthesis from propylene, carbon monoxide, and water or an alcohol in hydrogen fluoride under pressure, the reaction mixture, after reaction, is depressurized, a principal amount of the gaseous components to be removed is separated, the remaining liquid phase is introduced into the middle to upper region of a distillation column in which base temperature is kept above the boiling point of isobutyric acid and the head temperature is kept near the boiling point of hydrogen fluoride, and isobutyric acid is removed as a liquid of high purity from a plate below the entrance of the feed.

2 Claims, No Drawings

METHOD FOR MAKING ISOBUTYRIC ACID

The present invention relates to a method for the continuous preparation of isobutyric acid by the Koch synthesis from about stoichiometric amounts of propylene, carbon monoxide, and water or an alcohol, under pressure in liquid hydrogen fluoride as a Koch catalyst.

THE PRIOR ART

The main features of such a method are known from European patent EP-B No. 0,031,886 and from PCT patent WO No. 83/02940. In EP-B No. 0,031,886 the working up of the reaction mixture in two distillation stages is proposed, In the first stage, HF, unreacted propylene, and low boiling byproducts such as isopropyl alcohol, isopropyl fluoride, isobutyric acid fluoride, isobutyric acid isopropyl ester, and diisopropylether, are to be distilled off over the head and returned to the reactor. For the separation of the remaining mixture of isobutyric acid, oligomers of propylene, and other high boiling compounds, a second distillation column is provided from which isobutyric acid is taken off as the head product. WO No. 83/02940 also considers two distillation stages as unavoidable.

The performance of such a continuous process on a technical scale under economic conditions presents problems which arise from the demand for higher purity of the products of the method, that is for a very extensive separation of the reaction mixture on the one hand and from the demand for the slightest possible expenditure for apparatus and energy input.

In principal the demand for higher purity for the components to be separated from a reaction mixture is easy to satisfy if a suitable separation stage is provided for every component. In this way, mixtures of a plurality of volatile components can be separated into high boiling and low boiling components, with the required purity being provided by a suitable plate number in the rectification column and stripping column and by a suitable reflux ratio. But for mixtures of numerous components and where high purity is demanded, this leads to an expenditure for apparatus and for heating energy which is economically insupportable.

THE PROBLEM AND ITS SOLUTION

The problem thus existed to make do with only one distillation stage in a continuous method of the aforementioned kind while nevertheless obtaining isobutyric acid free of hydrogen fluoride and with only minimal high boiling impurities.

According to the invention, this problem is solved if the reaction mixture is depressurized after successful reaction, the main portion of the gaseous components is separated, and the remaining liquid phase is introduced into the middle to upper region of a distillation column and is removed from a lower plate as a liquid, whereby the base temperature is maintained above the boiling point of isobutyric acid and the head temperature is kept near the boiling point of hydrogen fluoride, in each case under the prevailing pressure.

PERFORMANCE OF THE INVENTION

The Koch synthesis of isobutyric acid in hydrogen fluoride as the Koch catalyst takes place in a heterogeneous reaction mixture under pressure. The reaction mixture consists of a liquid phase, which consists essentially of hydrogen fluoride. The gas phase principally contains carbon monoxide and a portion of hydrogen fluoride corresponding to its vapor pressure at the reaction temperature. The content of propylene is as a rule extremely small in both phases. This composition is independent of whether propylene, carbon monoxide, water, and hydrogen fluoride are added continuously as such or in the form of binary or ternary addition products such as isopropanol or isopropyl formate.

In a continuous method a portion of the reaction mixture is suitably removed from a location in the lower region of the reaction where the content of dispersed gas phase is small, so that what is removed consists mainly of the liquid phase. On depressurizing, the mixture separates spontaneously into a gas phase which predominately consist of hydrogen fluoride, dissolved carbon monoxide, and to a lesser extent of gaseous impurities and low boiling compounds, and into a liquid phase. The latter contains, in addition to isobutyric acid and hydrogen fluoride as its main components, all the high boiling compounds and amounts, corresponding to their solubility, of the components found in the gas phase.

According to the invention, the remaining liquid phase is resolved in a distillation column into at least three fractions, namely hydrogen fluoride as the head product, isobutyric acid containing high boiling compounds as the base product, and almost pure isobutyric acid as a side stream.

The column head is kept near the boiling point of hydrogen fluoride, under the pressure prevailing at the column head, by measures known in the art of continuous distillation. In this way, nearly pure hydrogen fluoride, possibly together with traces of gaseous impurities and slight amounts of isopropyl fluoride, is taken off at the column head. The deviation from the boiling point of pure hydrogen fluoride depends on the amount of these accompanying products and generally amounts to 1 or 2 degrees Kelvin at the most. The pressure at the column head is preferably set at 0.5 to 120 bars so that a head temperature of 0° C. to 90° C. results.

The column base is kept at a temperature above the boiling point of isobutyric acid at the pressure there prevalent. The boiling point of the isobutyric acid in the aforementioned pressure region is between 135° C. and 248° C. The base temperature preferably is about 30 to 90 degrees Kelvin higher. In the base, there is a mixture containing a predominant fraction of isobutyric acid and a smaller amount, for example 5 to 50 percent by weight, of high boiling compounds. The base product is removed in such an amount that its level and its content of high boiling compounds remain about constant.

The feed to the distillation column is made in the middle to upper region. In this way a zone is established in a region between the feed and the base in which there is almost pure isobutyric acid. This is removed as a liquid from a plate in this region. The formation of this zone can be attributed to the fact that there are few or no components in the reaction mixture which have a boiling point near that of isobutyric acid. Thus, the low boiling compounds are practically fully removed in the aforementioned zone and the high boiling compounds are reduced according to the ratio of the reflux stream to the feed stream.

If reaction conditions are maintained in the reactor following the teachings of EP-B No. 0,031,886, only slight amounts of high boiling compounds form.

A reaction temperature of 80° C. to 160° C., a propylene content less than 1 percent by weight, a water content below 5 mole percent, and a dwell time of the liquid phase of less than 20 minutes are characteristic for this method. In this case, an isobutyric acid of corresponding high purity is obtained with the separation method according to the invention. The content of hydrogen fluoride is preferably below 100 ppm and the content of high boiling compounds below 1 percent by weight. A content of 100 to 500 ppm is attainable, for example.

What is claimed is:

1. A method for the continuous preparation of isobutyric acid by the Koch synthesis from about stoichiometric amounts of propylene, carbon monoxide, and water, under pressure and in liquid hydrogen fluoride as the Koch catalyst, which method comprises depressurizing the reaction mixture after reaction, separating undispersed gas phase created by said depressurization, said gas phase predominantly consisting of hydrogen fluoride and carbon monoxide with smaller amounts of gaseous impurities and low boiling compounds, introducing the remaining liquid phase containing dispersed gas phase into the middle to upper region of a distillation column, and removing liquid isobutyric acid from a lower plate of the column, the head of said column being kept at a pressure of 0.5 to 120 bars so that a head temperature of 0° C. to 90° C. results, and the base of said column being kept at a temperature above the boiling point of isobutyric acid at the pressure which prevails.

2. A method as in claim 1 wherein isobutyric acid is removed from a plate at which the stationary concentration of hydrogen fluoride is less than 100 parts per million, the ratio of the reflux stream in the column to the feed stream being such that the stationary concentration of materials which boil at a temperature higher than isobutyric acid is less than one percent by weight at the plate from which isobutyric acid is removed.

* * * * *